Figure 1:
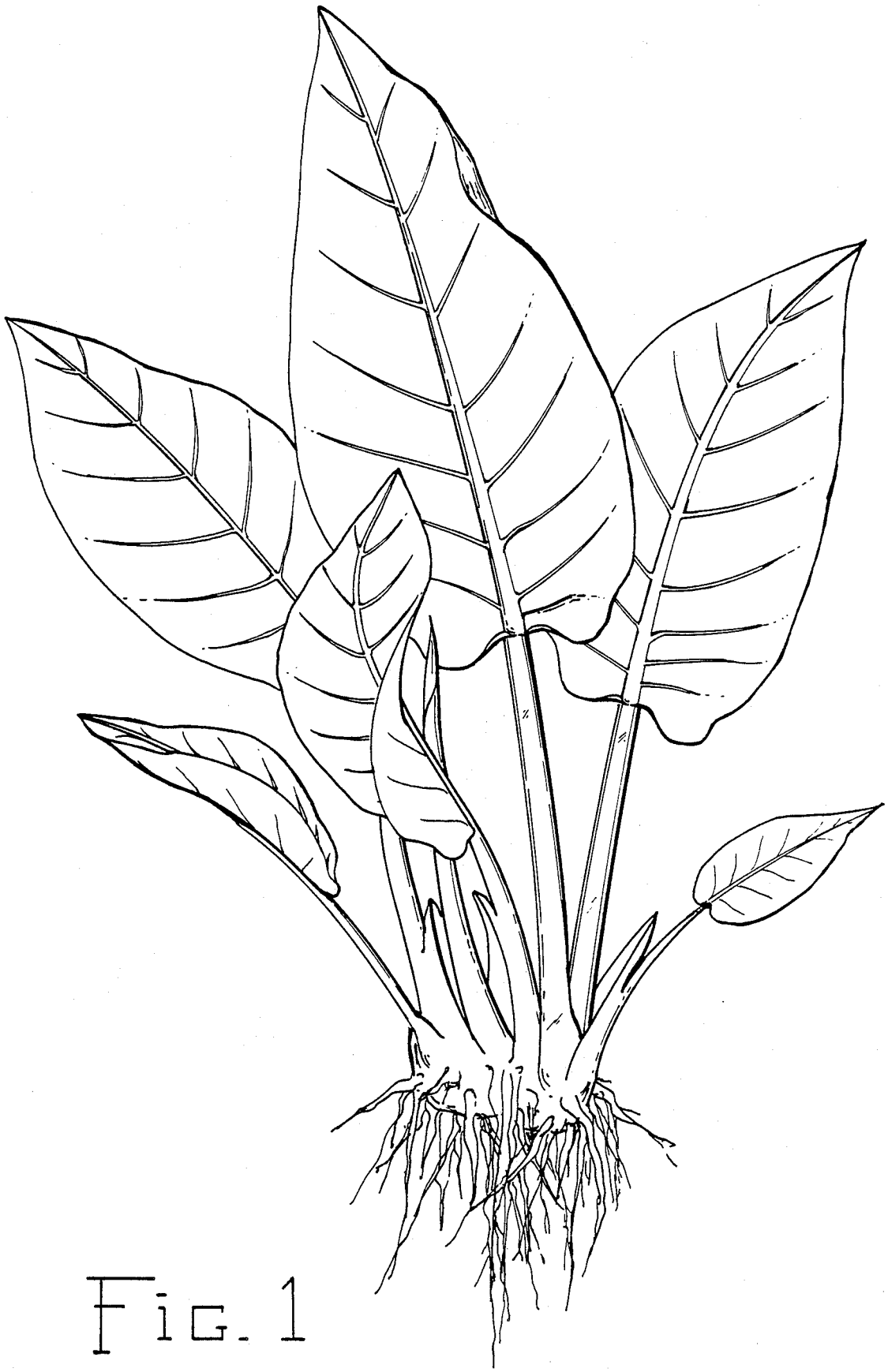

United States Patent [19]

Miller

[11] Patent Number: Plant 6,489

[45] Date of Patent: Dec. 27, 1988

[54] PHILODENDRON PLANT

[75] Inventor: Howard N. Miller, Gainesville, Fla.

[73] Assignee: Cora McColley, Orlando, Fla.

[21] Appl. No.: 34,625

[22] Filed: Apr. 6, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

The disclosure hereof is of a very compact, self-heading Philodendron plant of unusual density of growth. The plant is very stocky, producing an abundance of off-shoots from the crown, leaves are emerald green and are thick and glossy, having short thick petioles.

2 Drawing Sheets

BACKGROUND AND DESCRIPTION OF THE INVENTION

My present invention comprises a new and distinct variety of Philodendron plant which is the result of crossing *Philodendron canifolium* with an unnamed rosette seedling whose parentage includes *Philodendron hastatum, Philodendron erubescens, Philodendron wendlandi* and *Philodendron imbe.* From this cross a single seedling was selected for propagation and is the embodiment of this invention.

An extensive program of Philodendron hybridization has been carried on in the vicinity of Orlando, Fla. and is being continued. Much of the effort is directed toward developing tough, leathery, Philodendron which are compact, self-heading, excellent growers and keepers under in-house environments.

With the increasing emphasis on interior landscaping, there is great demand for new types of Philodendron with distinctive color, form and growth habit. The on-going breeding program has these objectives as a goal. The Philodendron of the instant invention is a compact self-heading plant of distinctive form, leaf type and color which approaches many of the above objectives. I have chosen to call it "Emerald Prince" for commercial identification.

I have caused the new variety to be asexually reproduced from crown off-shoots. Since the plant is compact, self-heading, and essentially has no stem, vegetative propagation is not commercially feasible. The plant can be mass produced by tissue culturing, and has been found to retain its distinctive characteristics through successive asexual reproduction.

My new variety has been grown under various conditions in several locations and having maintained its form and color given a wide range of light, temperature and moisture, is considered to be a good indoor foliage plant.

The new plant is distinctive from other Philodendrons in cultivation and is not described by Graf, Bailey or Das Pflanzenreich. While my new variety has some of the characteristics of certain species and hybrids, in most respects it is substantially different as comparisons with other species and varieties clearly disclose.

The new variety is a very compact rosette as compared with other rosette varieties of Philodendron which I have introduced. However, this variety is emerald green, even more compact and branches much more freely. There are other differences which are noted hereinafter and provide further distinctiveness.

The new variety is visually distinguished by the leaves, the mature leaves being narrowly ovate with cordate base and acute tip. The mature leaves are restricted near the base and the margins are entire.

Pinnate venation with large flattened prominent midribs are notable as are the thick, leathery and glossy emerald green color. The width of the leaf is approximately one-half the length.

The petioles are semi-erect to erect, round, thick with flat, slightly concave upper surface. On immature plants the petioles are enlarged at the base and are winged, being approximately three-fourths the length of the leaves. The internodes are one-half inch or less.

The most distinctive aspect of the new variety is its growth habit, low maintenance requirements and its keeping quality.

Since my new variety is a true rosette and essentially without a stem, it is very compact. Older plants may have a short stalk, but the petioles are superimposed on top of each other typically forming a plant that is twice as wide as it is high. Since this plant branches freely from the crown, especially from tissue culturing, a single plant will usually fill the container by the time it reaches saleable size. Growth is uniform and of good substance, and under good growing conditions is fast, but the plant does not become leggy. The average height of year old plants is 18"-20" with a width of 36"-40". Growth of micro cuttings and young plants is rapid.

The growth of the plant indoors is excellent. It is a good specimen plant, tolerates adverse conditions and retains its desired form longer than many Philodendrons known to be currently available. This new variety is resistant to bacterial leaf rot and fungal leaf spots.

I have established that my new variety will survive three to four weeks under normal in-house conditions without watering, does not wilt, and does not suffer any damage. In fact, the plant performs best indoors with minimum care. Since this is a compact, self-heading plant, it is only practically asexually produced from tissue culturing for commercial purposes and retains its distinctive characteristics through successive reproduction in this manner.

Figure 2:
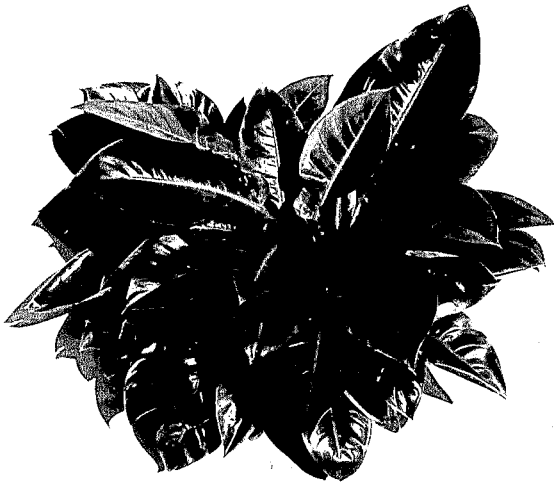

The accompanying drawings, forming a part of this disclosure, show a typical plant of the new variety in black and white in FIG. 1 and depicted in color in FIG. 2, with the colors being as nearly true as it is reasonably possible to make the same in color illustrations of this character.

Color references are made to the Munsell color cascade published by MacBeth of Kollmorgen Company, with observations recorded by daylight illumination under vinyl of not more than 30% shade.

FORM CHARACTERISTICS

1. Leaf shape:
   a. *Mature.*—Broadly ovate.
   b. *Immature.*—Narrowly ovate.
   c. *Tip.*—Acute.
   d. *Base.*—(1) Mature: Cordate. (2) Immature: Cordate.
   e. *Displacement.*—Smooth.
   f. *Margin.*—Entire-Restricted near base.
   g. *Veination.*—Pinnate, sunken; broad; flat prominent midribs.
2. Leaf attachment: Petiolate.
3. Leaf arrangement: Alternate; horizontal to slightly vertical.
4. Petiole: Three-fourths leaf length semi-erect to erect, round, thick, flat slightly concaved upper surface; in immature plants, enlarged at base and winged.
5. Stem: Very short, stocky.
6. Overall appearance: Very compact, self-heading, free standing.

Leaf texture characteristics: Firm, thick, leathery and glossy.

SIZE CHARACTERISTICS OF TYPICAL MATURE PLANT

1. Leaf:
   a. *Width-Widest point.*—6″-7″.
   b. *Width-1″ from top.*—1½″-2″.
   c. *Length.*—12″-13″.
   d. *Thickness.*—0.10 cm.
2. Petioles:
   a. *Length.*—6″-7″.
   b. *Diameter (center).*—½″.
   c. *Internode spacing.*—½″.
   d. *Stem diameter.*—1″.

COLOR CHARACTERISTICS

1. Leaf (mature):
   a. *Top.*—20-15 Dark emerald green.
   b. *Bottom.*—22-12 Olive green.
2. Leaf (immature):
   a. *Top.*—22-12 Olive green.
   b. *Bottom.*—22-11 Light olive green.
3. Leaf venation:
   a. *Midribs.*—21-13 Olive green.
   b. *Veins.*—21-14 Dark olive green.
4. Stem: 21-14 Dark olive green.
5. Petioles: 21-14 Dark olive green.

I claim:

1. A new and distinct variety of Philodendron plant, substantially as herein shown and described, characterized particularly as to novelty by its thick, ovate, waxy emerald green leaves, its self-heading growth habit and profuse branching from the crown, its excellent in-house growth, having the ability to withstand moderately low light, low maintenance and long periods without water, greater resistance to bacterial leaf rot than Philodendron varieties now available, and upright symmetrical growth, attaining an average height of 18″ to 20″ and width of 36″ to 40″ in approximately a year from tissue culture.

* * * * *